Feb. 18, 1969 MARIE-LOUISE MEILLAND Plant Pat. 2,862
ROSE PLANT
Filed Aug. 25, 1967
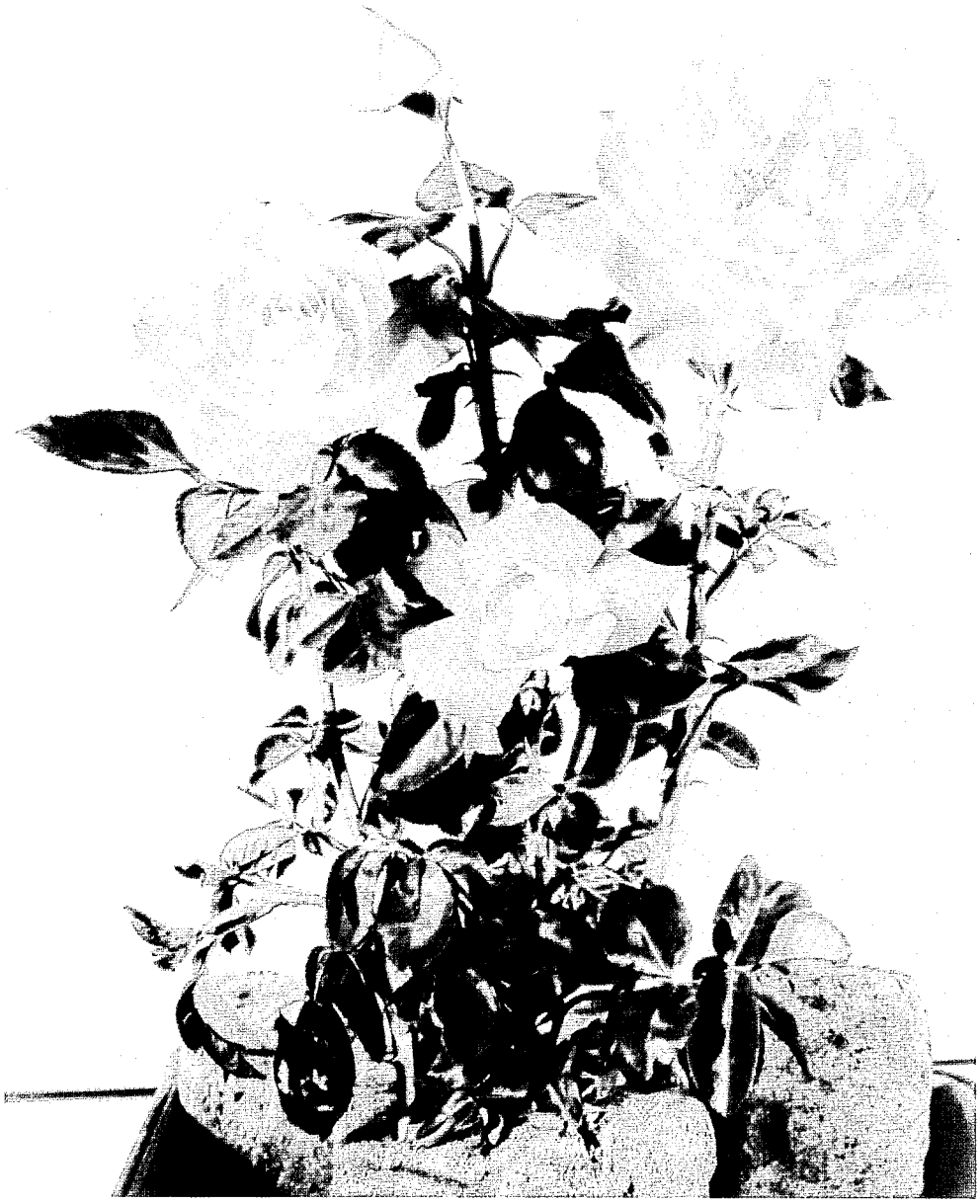

United States Patent Office

Plant Pat. 2,862
Patented Feb. 18, 1969

2,862
ROSE PLANT

Marie-Louise Meilland, Cap d'Antibes, France

Filed Aug. 25, 1967, Ser. No. 663,456
U.S. Cl. Plt.—11 1 Claim
Int. Cl. A01h 5/02

ABSTRACT OF THE DISCLOSURE

A variety of rose plant originated by crossing Suspense (Plant Patent No. 1,944) with Confidence (Plant Patent No. 1,192).

*Description of the invention*

This invention relates to a new and distinct variety of rose plant of the hybrid tea class which was originated by me by crossing Suspense (Plant Patent No. 1,944) with Confidence (Plant Patent No. 1,192).

The primary objective of this breeding was to create a distinct variety of rose different from all other known varieties of roses in several important characteristics.

This rose differs from its seed parent Suspense by having a better habit of growth which is more freely branched and with larger petals in the bloom more loosely cupped.

As compared to its pollen parent Confidence, the bloom is quite different by being more highly colored with carmine tones in the flower and by the bright green almost waxy foliage covering straight, stiff stems.

Asexual reproduction of my new variety by budding was performed in West Grove, Pa.

The accompanying drawing shows typical specimens of the flowers and foliage of my variety in different stages of development and as depicted in color as nearly true as is reasonably possible to make the same in a color illustration of this character.

The following is a detailed description of my new variety with color terminology in accordance with the horticultural color chart of the Royal Horticultural Society:

Type: Hardy; medium tall bush, outdoor; seedling; garden decoration.

Class: Hybird tea.

Propagation: It does hold its distinguishing characteristics through succeeding propagations by budding.

*The flower*

Locality where grown: West Grove, Pa.

Flowers borne: Singly; strong; long stems.

Quantity of bloom: Free, outdoors.

Continuity: Continuous.

Fragrance: Slight; tea.

Bud:

*Peduncle.*—Short; heavy; erect-stiff; medium green; entirely smooth.

*Before calyx breaks.*—Size—medium. Form—pointed; with appendages on the surface of the bud; with slender medium cut parts extending beyond the tip of the bud equal to ½ of its length.

*As calyx breaks.*—Color—Barium Yellow 503 with random coloring of carmine 21/1 at petal edge.

*As first petal opens.*—Size—large. Form—medium pointed. Color: outside—Naples Yellow 403/2 shaded with Scarlet 19/2 at petal edges; Mimosa Yellow 602 at very base occasional random streaking with Crimson 22/2; inside—Turkey Red 721/2; Canary Yellow 2 at lower ¼ of petal. Opening—does open up well.

Bloom:

*Size when fully open.*—Large, 4 to 5 inches.

*Petalage.*—Very double; from 40 to 50 petals; arranged regularly.

*Form.*—Full to high-centered at first; becoming cupped; petals remaining at first loosely rolled outward; becoming later at maturity cupped outward.

Petals: Thick; with inside satiny; outside velvety.

*Shape.*—Outer—obovate; apex pointed. Intermediate—obovate; apex pointed. Inner—obovate; with 1 to 3 notches; apex pointed.

*Color.*—Blotched.

This description of a newly opened flower was made from a rose grown outdoors in June 1967 at West Grove, Pa.

*Color.*—Outer petal: outside surface—Naples Yellow 403/3 blotched with Rose Madder 23/1; Canary Yellow 2/1 at point of attachment; inside surface—Tyrian Rose 24; lower ¼ shading to Canary Yellow 2/3. Canary Yellow 2 at point of attachment. Intermediate petal: outside surface—Lemon Yellow 4/2 shading to Canary Yellow 2/1; petal margined with near Begonia 619/1; inside surface—Carmine 21 over ¾ of petal; Canary Yellow 2 over lower ¼ of petal. Inner petal: outside surface—Lemon Yellow 4/2; Lemon Yellow 4/1 at a point of attachment; petal edges lightly tinted with Poppy Red 16/2; inside surface—Orient Red 819/3; Canary Yellow 2 over lower ¼ of petal.

This description was made from a rose that was open for three days, outdoors in June 1967 at West Grove, Pa.

*Color.*—Outer petal: outside surface—lighter than Egyptian Buff 407/3 shading to Sulphur Yellow 1/3 at petal base; petal edges and occasional random blotching Sulphur Yellow 1/3 at petal base; inside surface—Rose Bengal 25/1; near Primrose Yellow 601/3 over lower ¼ of petal; Sulphur Yellow 1/1 at point of attachment. Inner petal: outside surface—Naples Yellow 403/1 lightly tinted at petal margin with near Begonia 619/2; Sulphur Yellow 1/1 at point of attachment; inside surface—Carmine 21/1; lower ¼ of petal Canary Yellow 2/2 shading to Canary Yellow 2/1 at base.

*General color effect.*—Newly opened flower—bicolor rose: under sides and base of upper sides of petals near Naples Yellow 403/1; upper sides of petals Crimson 22/1. Three days open—bicolor rose: upper surface near China Rose 024/1; under surface near Naples Yellow 403/3.

*Behavior.*—Drop off cleanly; colors may deepen in cooler weather.

*Flower longevity.*—On bush in garden 5 days in June; cut roses kept at living room temperatures 4 days in June.

*Reproductive organs*

Stamens: Many; arranged regularly about pistils mixed with occasional petaloids.

Filaments: Many, with anthers; long. Color—Sulphur Yellow 1.

Anthers: All open at once; large. Color—Sulphur Yellow 1/3; occasionally an anther fused with a petaloid.

Pollen: Abundant; gold.

Pistils: Many.

Styles: Uneven; short; medium, bunched.

Sigma: White.

Ovaries: All enclosed.

Hips: None observed.

Sepals: Permanent; medium, spear-shaped.

*Plant*

Foliage:

*Leaves.*—Compound of 5 to 7; normal; large; glossy.

*Leaflets.*—Shape—ovoid with apex acute; base obtuse doubly serrate.

*Color.*—Mature: upper surface—Parsley Green 00962; under surface—Willow Green 000862/1. Young: upper surface—near Parsley Green 00962/3 with some maroon (general color term) at margin; under surface—near Scheeles Green 860/3 lightly shaded with maroon (general color term) at leaflet edges.

*Rachis (the supporting stem of the compound leaf).*—Heavy. Upper side—grooved red, glandular tipped hairs along sides. Under side—moderately thorny.

*Stipules.*—Long; narrow; with long points; turning out at an angle of more than 45°.

*Disease.*—Resistance comparable to the average variety growing under the same cultural conditions.

Growth:

*Habit.*—Bushy upright.

*Growth.*—Free.

*Canes.*—Medium.

*Main stems.*—Dull; color—Spinach Green 0960/2. Prickles—many; color—near Uranium Green 63/2. Hairs—several; color—white (general color term).

*Branches.*—Dull; color—Spinach Green 0960/1. Prickles—many; color—Lettuce Green 861/1. Hairs—several; color—white (general color term).

*New shoots.*—Dull; color—near Lettuce Green 861/2. Prickles—several; color—near Pod Green 061. Hairs—several; color—white (general color term).

I claim:

1. A new and distinct variety of rose plant of the hybrid tea class, substantially as herein shown and described, characterized particularly as to novelty by the unique combination of carmine and yellow coloring of the flower in a bicolor effect, the free branching of the vigorous, upright plant with heavy, stiff stems, well covered by large, bright green, waxy leaves and the free, continuous flowering habit and bloom form and color which hold well under wide variations of weather.

No references cited.

ROBERT E. BAGWILL, *Primary Examiner.*